(12) United States Patent
Frederickson et al.

(10) Patent No.: US 10,315,021 B2
(45) Date of Patent: Jun. 11, 2019

(54) COLLAPSIBLE PATCH AND METHOD OF APPLICATION

(71) Applicant: 3M INNOVATIVE PROPERTIES COMPANY, St. Paul, MN (US)

(72) Inventors: Franklyn L. Frederickson, Grand Rapids, MN (US); Michael D. Johnson, College Station, TX (US); David J. Wirtanen, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/608,620

(22) Filed: May 30, 2017

(65) Prior Publication Data
US 2017/0258713 A1    Sep. 14, 2017

Related U.S. Application Data

(63) Continuation of application No. 11/917,300, filed as application No. PCT/US2006/024673 on Jun. 23, 2006, now abandoned.

(60) Provisional application No. 60/693,901, filed on Jun. 24, 2005.

(51) Int. Cl.
*A61M 37/00* (2006.01)
*A61K 9/00* (2006.01)

(52) U.S. Cl.
CPC ....... *A61M 37/0015* (2013.01); *A61K 9/0021* (2013.01); *A61M 2037/0023* (2013.01)

(58) Field of Classification Search
CPC ...... A61M 37/0015; A61M 2037/0023; A61M 2037/003; A61M 2037/0038; A61M 2037/0046; A61M 2037/0061; A61M 2005/3258; A61K 9/0021
See application file for complete search history.

(56) References Cited

U.S. PATENT DOCUMENTS

| | | | |
|---|---|---|---|
| 2,619,962 | A | 12/1952 | Rosenthal |
| 3,034,507 | A | 5/1962 | McConnell et al. |
| 3,072,122 | A | 1/1963 | Rosenthal |
| 3,123,212 | A | 3/1964 | Taylor et al. |
| 3,136,314 | A | 6/1964 | Kravitz |
| RE25,637 | E | 9/1964 | Kravitz et al. |
| 3,221,740 | A | 12/1965 | Rosenthal |
| 3,246,647 | A | 4/1966 | Taylor et al. |

(Continued)

FOREIGN PATENT DOCUMENTS

| | | |
|---|---|---|
| EP | 407063 | 1/1991 |
| GB | 1080986 | 8/1967 |

(Continued)

OTHER PUBLICATIONS

"Collapsible". Merriam-Webster Online Dictionary. <http://www.merriam-webster.com/dictionary/collapsible>.

(Continued)

*Primary Examiner* — Kami A Bosworth
(74) *Attorney, Agent, or Firm* — Eric E. Silverman

(57) ABSTRACT

A microneedle patch includes a base, at least one collapsible side wall extending from the base, and a lip disposed along the at least one collapsible sidewall and opposite the base. An adhesive is disposed along the base, and a microneedle array is affixed to the base.

9 Claims, 10 Drawing Sheets

(56) References Cited

U.S. PATENT DOCUMENTS

| | | | |
|---|---|---|---|
| 3,322,121 A | 5/1967 | Banker | |
| 3,466,131 A | 9/1969 | Arcudi | |
| 3,510,933 A | 5/1970 | Taylor et al. | |
| 3,512,520 A | 5/1970 | Cowan | |
| 3,596,660 A | 8/1971 | Melone | |
| 3,675,766 A | 7/1972 | Rosenthal | |
| 3,678,150 A | 7/1972 | Szumski et al. | |
| 3,688,764 A | 9/1972 | Reed et al. | |
| 3,905,371 A | 9/1975 | Stickl et al. | |
| 3,964,482 A | 6/1976 | Gerstel et al. | |
| 4,109,655 A | 8/1978 | Chacornac | |
| 4,237,906 A | 12/1980 | Havstad et al. | |
| 4,304,241 A | 12/1981 | Brennan | |
| 4,360,016 A | 11/1982 | Sarrine | |
| 4,453,926 A | 6/1984 | Galy | |
| 4,473,083 A | 9/1984 | Maganias | |
| 4,503,856 A | 3/1985 | Cornell et al. | |
| 4,517,978 A | 5/1985 | Levin et al. | |
| 4,637,403 A | 1/1987 | Garcia et al. | |
| 4,735,618 A * | 4/1988 | Hagen | A61M 5/3275 604/110 |
| 4,858,607 A | 8/1989 | Jordan et al. | |
| 4,869,249 A | 9/1989 | Crossman et al. | |
| 4,920,977 A | 5/1990 | Haynes | |
| 4,921,475 A | 5/1990 | Sibalis | |
| 4,924,879 A | 5/1990 | O'Brien | |
| 5,015,240 A * | 5/1991 | Soproni | A61M 5/326 604/192 |
| 5,250,023 A | 10/1993 | Lee et al. | |
| 5,318,584 A | 6/1994 | Lange et al. | |
| 5,368,047 A | 11/1994 | Suzuki et al. | |
| 5,402,798 A | 4/1995 | Swierczek et al. | |
| 5,487,726 A | 1/1996 | Rabenau et al. | |
| 5,611,806 A | 3/1997 | Jang | |
| 5,879,326 A | 3/1999 | Godshall et al. | |
| 5,983,136 A | 11/1999 | Kamen | |
| 6,050,988 A | 4/2000 | Zuck | |
| 6,091,975 A | 7/2000 | Daddona et al. | |
| 6,126,637 A * | 10/2000 | Kriesel | A61M 5/152 604/132 |
| 6,132,755 A | 10/2000 | Eicher et al. | |
| 6,256,533 B1 | 7/2001 | Yuzhakov et al. | |
| 6,293,925 B1 | 9/2001 | Safabash et al. | |
| 6,312,612 B1 | 11/2001 | Sherman et al. | |
| 6,322,808 B1 | 11/2001 | Trautman et al. | |
| 6,334,856 B1 | 1/2002 | Allen et al. | |
| 6,379,324 B1 | 4/2002 | Gartstein et al. | |
| 6,440,096 B1 | 8/2002 | Lastovich et al. | |
| 6,454,755 B1 | 9/2002 | Godshall | |
| 6,503,231 B1 | 1/2003 | Prausnitz et al. | |
| 6,532,386 B2 | 3/2003 | Sun et al. | |
| 6,537,242 B1 | 3/2003 | Palmer | |
| 6,589,202 B1 | 7/2003 | Powell | |
| 6,591,124 B2 | 7/2003 | Sherman et al. | |
| 6,595,947 B1 | 7/2003 | Mikszta et al. | |
| 6,603,998 B1 | 8/2003 | King et al. | |
| 6,611,707 B1 | 8/2003 | Prausnitz et al. | |
| 6,623,457 B1 | 9/2003 | Rosenberg | |
| 6,656,147 B1 | 12/2003 | Gertsek et al. | |
| 6,689,100 B2 | 2/2004 | Connelly et al. | |
| 6,689,103 B1 * | 2/2004 | Palasis | A61B 17/3207 604/173 |
| 6,713,291 B2 | 3/2004 | King et al. | |
| 6,743,211 B1 | 6/2004 | Prausnitz et al. | |
| 6,797,276 B1 | 9/2004 | Glenn et al. | |
| 6,855,131 B2 | 2/2005 | Trautman et al. | |
| 6,881,203 B2 | 4/2005 | Delmore et al. | |
| 6,890,319 B1 | 5/2005 | Crocker | |
| 6,908,453 B2 | 6/2005 | Fleming et al. | |
| 6,931,277 B1 | 8/2005 | Yuzhakov et al. | |
| 2002/0032415 A1 | 3/2002 | Trautman et al. | |
| 2002/0082543 A1 | 6/2002 | Park et al. | |
| 2002/0087182 A1 | 7/2002 | Trautman et al. | |
| 2002/0091357 A1 | 7/2002 | Trautman et al. | 604/117 |
| 2002/0095134 A1 | 7/2002 | Pettis et al. | |
| 2002/0102292 A1 | 8/2002 | Cormier et al. | |
| 2002/0111600 A1 | 8/2002 | Cormier et al. | |
| 2002/0123675 A1 | 9/2002 | Trautman et al. | |
| 2002/0128599 A1 | 9/2002 | Cormier et al. | |
| 2002/0138049 A1 | 9/2002 | Allen et al. | |
| 2002/0169416 A1 | 11/2002 | Gonnelli et al. | |
| 2002/0177839 A1 | 11/2002 | Cormier et al. | |
| 2002/0177858 A1 | 11/2002 | Sherman et al. | |
| 2002/0188245 A1 | 12/2002 | Martin et al. | |
| 2002/0193729 A1 | 12/2002 | Cormier et al. | |
| 2002/0198509 A1 | 12/2002 | Mikszta et al. | |
| 2003/0036710 A1 | 2/2003 | Matriano et al. | |
| 2003/0045837 A1 | 3/2003 | Delmore et al. | |
| 2003/0050602 A1 | 3/2003 | Pettis et al. | |
| 2003/0083641 A1 | 5/2003 | Angel et al. | |
| 2003/0135158 A1 | 7/2003 | Gonnelli | |
| 2003/0149404 A1 * | 8/2003 | Lehmann | A61M 5/326 604/198 |
| 2003/0168366 A1 * | 9/2003 | Hirsiger | A61M 5/326 206/365 |
| 2003/0181863 A1 | 9/2003 | Ackley et al. | |
| 2003/0187394 A1 | 10/2003 | Wilkinson et al. | |
| 2003/0199812 A1 | 10/2003 | Rosenberg | |
| 2003/0208167 A1 | 11/2003 | Prausnitz et al. | |
| 2004/0039343 A1 | 2/2004 | Eppstein et al. | |
| 2004/0049150 A1 | 3/2004 | Dalton et al. | |
| 2004/0077994 A1 | 4/2004 | Lastovich et al. | |
| 2004/0106904 A1 | 6/2004 | Gonnelli et al. | |
| 2004/0116865 A1 * | 6/2004 | Bengtsson | A61M 5/14248 604/171 |
| 2004/0138612 A1 | 7/2004 | Shermer et al. | |
| 2004/0176732 A1 | 9/2004 | Frazier et al. | |
| 2004/0181203 A1 | 9/2004 | Cormier et al. | |
| 2005/0025778 A1 | 2/2005 | Cormier et al. | |
| 2005/0027242 A1 | 2/2005 | Gabel et al. | |
| 2005/0049549 A1 | 3/2005 | Wong et al. | |
| 2005/0065463 A1 | 3/2005 | Tobinaga et al. | |
| 2005/0065466 A1 | 3/2005 | Vedrine | |
| 2005/0065472 A1 | 3/2005 | Cindrich et al. | |
| 2005/0089554 A1 | 4/2005 | Cormier et al. | |
| 2005/0096586 A1 | 5/2005 | Trautman et al. | |
| 2005/0106226 A1 | 5/2005 | Cormier et al. | |
| 2005/0106227 A1 | 5/2005 | Zalipsky et al. | |
| 2005/0137525 A1 | 6/2005 | Wang et al. | |
| 2005/0261631 A1 | 11/2005 | Clarke et al. | |
| 2006/0047242 A1 | 3/2006 | Laurent et al. | 604/46 |
| 2007/0049865 A1 * | 3/2007 | Radmer | A61M 5/14248 604/93.01 |

FOREIGN PATENT DOCUMENTS

| | | |
|---|---|---|
| GB | 2064329 | 6/1981 |
| GB | 2221394 | 2/1990 |
| WO | WO 96/10630 | 4/1996 |
| WO | WO 01/36037 | 5/2001 |
| WO | WO 01/93931 | 12/2001 |
| WO | WO 05/51455 | 6/2005 |
| WO | WO 05/51476 | 6/2005 |
| WO | WO 05/65765 | 7/2005 |
| WO | WO 05/123173 | 12/2005 |
| WO | WO 2006/055795 | 5/2006 |
| WO | WO 2007/075806 | 7/2007 |

OTHER PUBLICATIONS

"Collapse". The American Heritage Dictionary. <http://www.thefreedictionary.com/collapsed>.

Daddona. Current Opinion in Drug Discovery and Development 1999 2(2);168-171.

Kaushik et al. Anesthesia Analg., 2001, 92, 502-504.

Henry et al. J. Pharm.Sci., 1998, 87,8,922-925.

McAllister et al. Annual Review of Biomedical Engineering, 2000, 2, 289-313.

(56) References Cited

OTHER PUBLICATIONS

McAllister et al. Proceed. Int'l. Symp. Control Release of Bioactive Material, 26, (1999), CRS, 192-193.

* cited by examiner

COLLAPSIBLE PATCH AND METHOD OF APPLICATION

CROSS-REFERENCE TO RELATED APPLICATIONS

This application is a continuation of U.S. Ser. No. 11/917,300, filed Dec. 12, 2007, which is a national stage filing under 35 U.S.C. 371 of PCT/US2006/24673, filed Jun. 23, 2006, which claims the benefit of U.S. Provisional Patent Application No. 60/693,901, filed Jun. 24, 2005, the disclosure of which is incorporated by reference in their entirety herein.

FIELD

The present invention relates to microneedle patches and patch assemblies, and more particularly to collapsible microneedle patches and patch assemblies for carrying and delivering microneedle arrays.

BACKGROUND

Only a limited number of molecules with demonstrated therapeutic value can be transported through the skin via unassisted or passive transdermal drug delivery. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents, vaccines and other substances through the skin and other surfaces. The devices are typically pressed against the skin to deliver molecules to a particular location. Microneedles of these devices pierce the stratum corneum upon contact, making a plurality of microscopic slits which serve as passageways through which molecules of active components can be delivered into the body. In delivering an active component, the microneedle device can be provided with a reservoir for temporarily retaining an active component in liquid form prior to delivering the active component through the stratum corneum. In some constructions, the microneedles can be hollow to provide a liquid flow path directly from the reservoir and through the microneedles to enable delivery of the therapeutic substance through the skin. In alternate constructions, active component(s) may be coated on the microneedle array and delivered directly through the skin after the stratum corneum has been punctured.

Microneedle arrays can be used in conjunction with an applicator device capable of being used a number of different times. The microneedle arrays are generally used once and then discarded.

Microneedles can be delivered using a patch that carries the microneedles. The patches are typically manufactured in a flat sheet-like configuration, carrying the microneedles. Patches may be temporarily attached to a disposable collar for an applicator device using, for example, an adhesive. The disposable collar may then be temporarily attached to the applicator using, for example, a mechanical snap-fit.

Patches, with or without a microneedles, can have fragile and sanitary characteristics. It is generally desired that the patch and array not be touched before application to a target site. This presents difficulties in storing and transporting patches to desired locations for eventual application. The patches may be stored along with the collars. However, the collars are large, and storage of disposable collars takes up excessive space and generates excessive waste.

Thus, the present invention provides an alternative microneedle patch and patch assembly.

BRIEF SUMMARY

In a first aspect of the present invention, a microneedle patch includes a base, at least one collapsible side wall extending from the base, and a lip disposed along the at least one collapsible sidewall and opposite the base. An adhesive is disposed along the base, and a microneedle array is affixed to the base.

In another aspect of the present invention, a microneedle patch system includes a collapsible patch element having a base and at least one side wall extending from the base. The base of the collapsible patch element has an upper face and an opposite bottom face, and the at least one side wall generally extends from the bottom face of the base. A microneedle array is affixed to the bottom face of the base of the collapsible patch element, and a first carrier is disposed adjacent to the collapsible patch element and relative to the bottom face of the base. The first carrier covers the microneedle array, and is separable from the collapsible patch element.

In another aspect of the present invention, a microneedle patch assembly includes a web of material having an upper face and a lower face, an adhesive disposed along the lower face of the web of material, and a microneedle array affixed to the lower face of the web of material. The patch has a first state where the web of material defines a first volume relative to its lower face and the microneedle array is spaced from a target site. The patch also has a second state where the web of material defines a second volume that is less than the first volume and the microneedle array contacts the target site.

In another aspect of the present invention, a method of microneedle array deployment includes positioning a patch carrying a microneedle array relative to a target site and collapsing at least a portion of the patch while moving the microneedle array toward the target site.

In another aspect of the present invention, a method of microneedle array deployment includes positioning a patch carrying a microneedle array near a target site. The patch is initially in an expanded state and the microneedle array is spaced from the target site. The microneedle array is moved toward the target site by placing the patch in a collapsed state, where at least a portion of the patch is collapsed and the microneedle array contacts the target site. The patch is also adhered to the target site with an adhesive disposed on the patch.

In another aspect of the present invention, a microneedle patch assembly includes a patch element having, in an initial expanded state, a first skin contacting surface and a second surface spaced from the first surface. A microneedle array is affixed to the second surface of the patch element.

In another aspect of the present invention, a microneedle patch system includes a plurality of collapsible patch elements nested together to form a package. Each collapsible patch element includes a base having an upper face and an opposite bottom face, at least one side wall extending from the base, and a microneedle array affixed to the bottom face of the base. The at least one side wall generally extends from the bottom face of the base.

The above summary is not intended to describe each disclosed embodiment or every implementation of the pres-

While the above-identified drawing figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale. Like reference numbers have been used throughout the figures to denote like parts.

DETAILED DESCRIPTION

Patches can be used for transdermal delivery of molecules, and can carry microneedle arrays, which have utility for the delivery of large molecules that are ordinarily difficult to deliver by passive transdermal delivery. As used herein, "array" refers to the medical devices described herein that include one or more structures capable of piercing the stratum corneum to facilitate the transdermal delivery of therapeutic agents or the sampling of fluids through or to the skin. "Microstructure," "microneedle" or "microarray" refers to the specific microscopic structures associated with the array that are capable of piercing the stratum corneum to facilitate the transdermal delivery of therapeutic agents or the sampling of fluids through the skin. By way of example, microstructures can include needle or needle-like structures as well as other structures capable of piercing the stratum corneum. The microneedles are typically less than 500 microns in height, and sometimes less than 300 microns in height. The microneedles are typically more than 20 microns in height, often more than 50 microns in height, and sometimes more than 125 microns in height.

Figure 1:
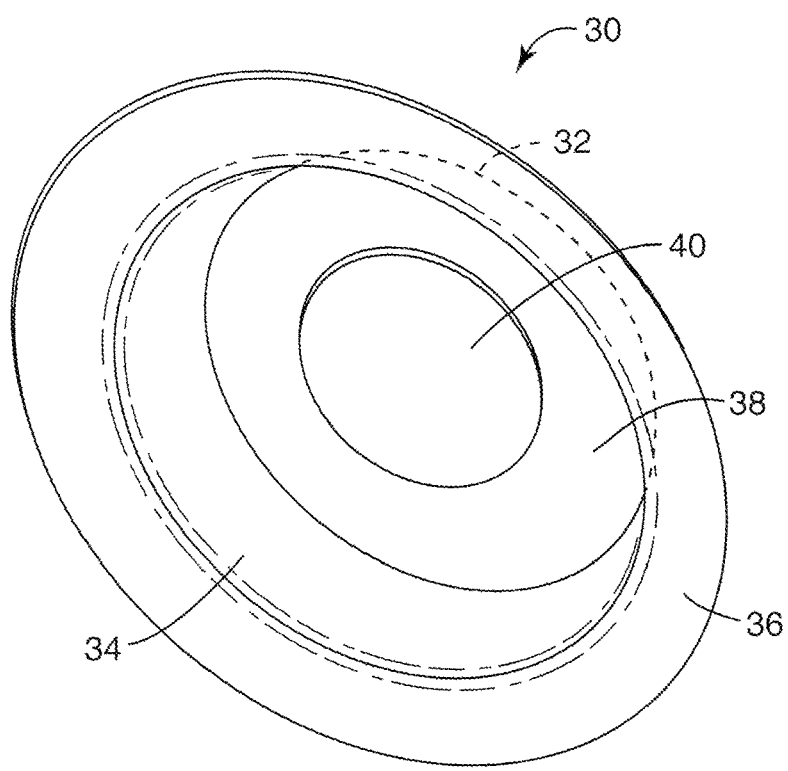
FIG. 1 is a perspective bottom view of a microneedle patch.
Figure 2A:
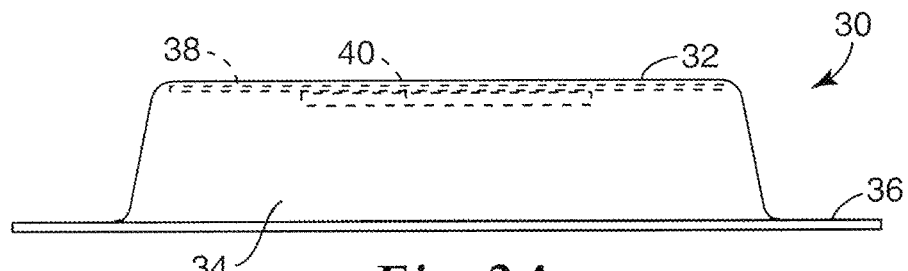
FIG. 2A is a side view of the microneedle patch of FIG. 1 in an expanded state.
Figure 2B:
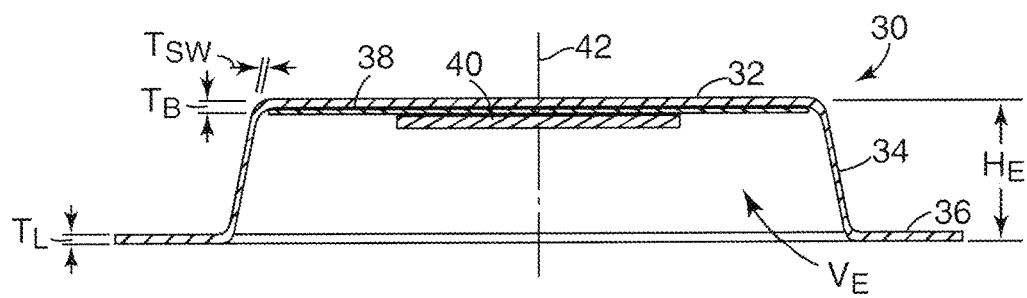
FIG. 2B is a cross-sectional view of the microneedle patch of FIGS. 1 and 2A in an expanded state.

FIGS. 1-2B and 3A-3B show a first embodiment of a collapsible microneedle patch 30 according to the present invention that has a first, expanded state and a second, collapsed state. FIG. 1 is a perspective view of the microneedle patch 30 in the expanded state. FIG. 2A is a side view of the microneedle patch 30 in the expanded state. FIG. 2B is a cross-sectional view of the microneedle patch 30 in the expanded state.

The microneedle patch 30 has a collapsible patch element comprising a generally circular base portion 32, at least one side wall 34 extending from the base portion 32, and a perimeter lip 36 extending from the side wall 34 opposite the base portion 32. The base portion 32, the side wall 34 and the perimeter lip 36 can be formed integrally. An adhesive 38 is disposed on the base portion 32, and a microneedle array 40 is supported by the base portion 32 (individual microneedles of the array 40 are not visible in the figures). As seen in FIG. 2B, the side wall 34 is disposed at an angle between the perimeter of the base portion 32 and the inner diameter of the perimeter lip 36, such that the inner diameter of the perimeter lip 36 is larger than the perimeter (i.e., the outer diameter) of the base portion 32 (measured with respect to an axis 42 defined at a center of the patch 30). In an alternative embodiment (not shown) the side wall may be generally perpendicular to the base and the lip, such that the inner diameter of the perimeter lip 36 would be about the same size as the perimeter of the base portion 32. In still another embodiment (not shown) the side wall may be angled such that the inner diameter of the perimeter lip 36 would be smaller than the perimeter of the base portion 32, although the inner diameter of the perimeter lip should be large enough to allow the microneedle array 40 to contact a target surface. The side wall 34 also generally has a smaller thickness $T_{SW}$ than thicknesses $T_B$ and $T_L$ of the base portion 32 and the perimeter lip 36, respectively. The patch may further comprise an adhesive (not shown in FIGS. 1-2B) disposed along the surface of the lip opposed to the base.

In one embodiment, the side wall thickness $T_{SW}$ is about 0.0001 inches (0.00254 mm) to about 0.010 inches (0.254 mm), and is preferably about 0.0005 inches (0.0127 mm) to about 0.005 inches (0.127 mm). The outer diameter of the perimeter lip 36 is typically about 1 inch (2.54 cm) to about 3 inches (7.62 cm), the outer diameter of the base portion 32 is typically about 0.5 inches (1.27 cm) to about 2.5 inches (6.35 cm). An overall height $H_E$ of the patch 30 (in the expanded state) is typically about 0.1 inches (0.254 cm) to about 1 inch (2.54 cm). In one embodiment, the base thickness $T_B$ is about 0.005 inches (0.127 mm) to about 0.050 inches (1.27 mm). In one embodiment, the lip thickness $T_L$ is about 0.005 inches (0.127 mm) to about 0.050 inches (1.27 mm).

The base portion 32 and the perimeter lip 36 are each generally planar. When the patch 30 is in the expanded state, the base portion 32 and the perimeter lip 36 are spaced from one another (i.e., are not coplanar). The base portion 32, the perimeter lip 36 and the side wall 34 define a volume $V_E$ relative to a bottom face of the patch 30. The patch 30 has enough rigidity to remain in the expanded state without undesired collapse prior to application, due to external factors such as gravity and slight inadvertent contact.

Figure 2C:
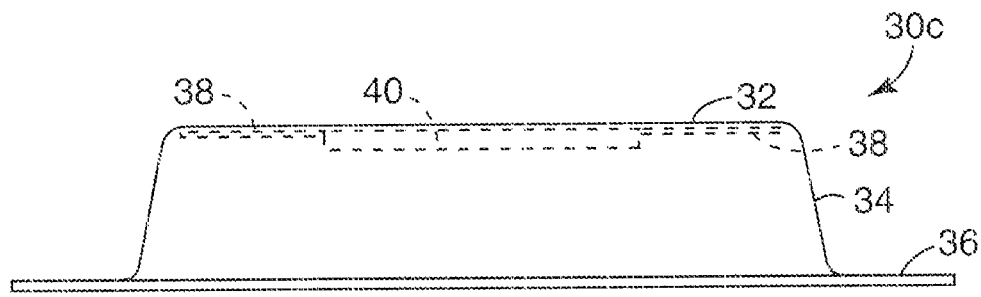
FIG. 2C is a side view of another embodiment of a microneedle patch in an expanded state.

In FIGS. 1-2B, the microneedle array 40 is affixed to the base portion 32 by the adhesive 38. Furthermore, the adhesive 38 extends along the base portion 32 beyond the microneedle array 40 and surrounds the microneedle array 40. The microneedle array 40 can also be connected to the base portion 32 in other ways. FIG. 2C is a side view of another embodiment of a microneedle patch 30C in the expanded state. As shown in FIG. 2C, the microneedle array 40 is connected to the base portion 32, without adhesive disposed therebetween. Such a connection can be made by processes such as welding and directly forming the microneedle array 40 on the base portion 32. As shown in FIG. 2C, the adhesive 38 is disposed on the base portion 32 around the microneedle array 40.

Figure 3A:
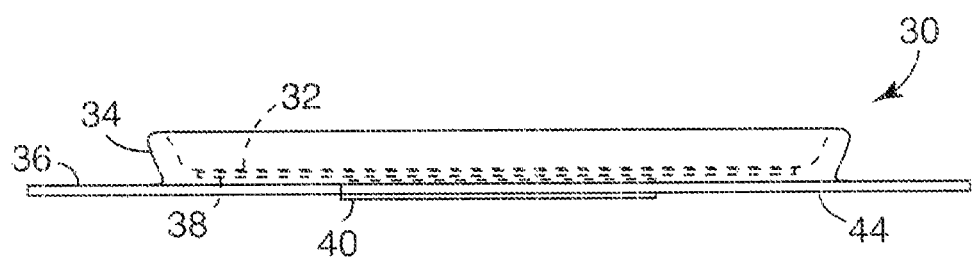
FIG. 3A is a side view of the microneedle patch of FIGS. 1-2B in a collapsed state.
Figure 3B:
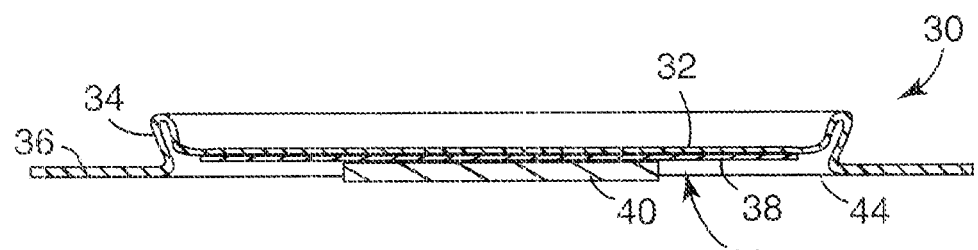
FIG. 3B is a cross-sectional view of the microneedle patch of FIGS. 1-2B and 3A in a collapsed state.

FIG. 3A is a side view of the microneedle patch 30 in the collapsed state. FIG. 3B is a cross-sectional view of the microneedle patch 30 in the collapsed state. In the collapsed state, the base portion 32 and the perimeter lip 36 are closer together than in the expanded state. In the collapsed state shown in FIGS. 3A and 3B, the microneedle array 40 extends at least as far, and preferably beyond, a skin-contacting face 44 of the perimeter lip 36 of the patch 30. The base portion 32, the perimeter lip 36 and the side wall 34 define a volume $V_C$, which is less than a volume $V_E$ defined in the expanded state.

Collapsing of the patch 30 involves deformation of a portion of the patch 30, for example, deforming the side wall 34. The relatively thin wall thickness $T_{SW}$ of the side wall 34 facilitates collapse of the patch 30, and allows increased predictability in the deformation pattern (i.e., the characterization of deformation of the patch 30 resulting from collapse) for increasing reliability of microneedle array 40 deployment. This deformation may take many forms, and FIGS. 3A and 3B are merely exemplary of this result. It should be recognized that other deformation patterns are possible.

At least the circular base portion 32, the side wall 34, and the perimeter lip 36 of the patch 30 are preferably formed of a thermoplastic material, such as polypropylene, polybutylene terephthalate, polystyrene, polyethylene, polythermide, polyethylene terephthalate, polystyrene, polyvinyl chloride, polymethylmethacrylate, acrylonitrile-butadiene styrene, polycarbonate, and blends thereof. Other possible materials include metal foils, such as aluminum, steel, and stainless steel. The base 32, side wall 34, and perimeter lip 36 may be made of a single material or they may be formed using separate materials.

Figure 4:
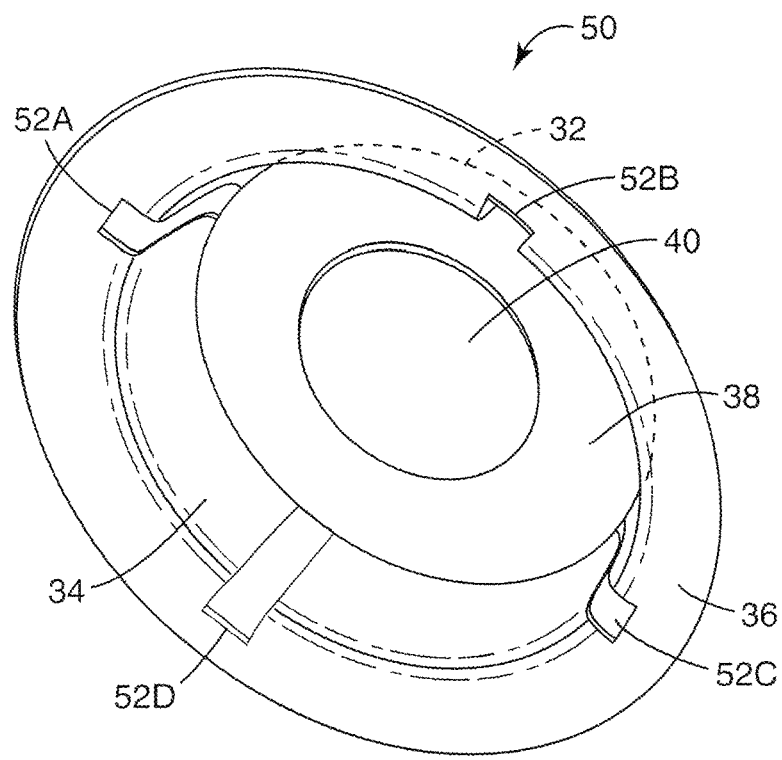
FIG. 4 is a perspective bottom view of another embodiment of a microneedle patch having slots defined therethrough.
Figure 5:
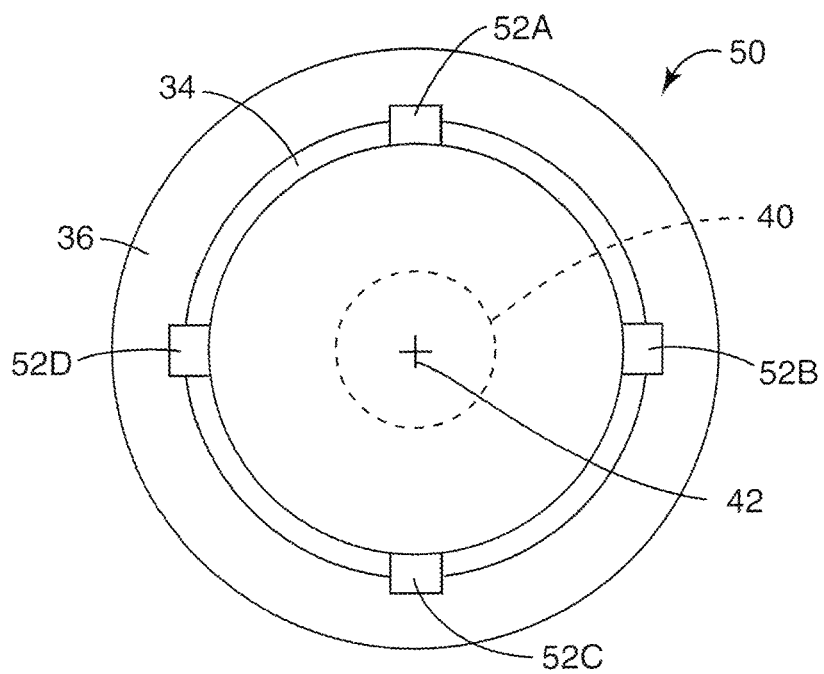
FIG. 5 is a top view of the microneedle patch of FIG. 4.

FIG. 4 is a perspective view of another embodiment of a microneedle patch 50 having a plurality of slots 52A-52D defined therethrough to form venting features. The microneedle patch 50 is generally similar to those shown and described with respect to FIGS. 1-3B. The slots 52A-52D are each generally elongated in shape, and extend from the base portion 32, along the side wall 34 and into the perimeter lip 36. FIG. 5 is a top view of the microneedle patch 50. In one embodiment, the slots 52A-52D may be spaced equally about axis 42. As shown in FIGS. 4 and 5, there are four slots 52A-52D and they are positioned 90° from each other with respect to axis 42.

The slots 52A-52D extend through the patch 50 to create openings or passageways, which permit air to pass through the side wall 34. Openings defined by the slots 52A-52D allow air to escape from the interior volume of the patch 50 as it collapses. This helps promote predictable movement of the microneedle array 40 during deployment, and helps reduce sound (e.g., a "popping" sound) generated during patch collapse. The sizes of each of the slots 52A-52D can be selected according to the amount of airflow desired during collapse of the patch 50. In addition, the slots 52A-52D can be pre-formed in the patch 50, or formed or cut into the patch 50 as part of a patch application process. In general, a vented system will have at least one air outlet defined in the collapsible patch element, so that it allows venting when the patch is placed against a continuous target surface and the patch volume is compressed.

Figure 6:
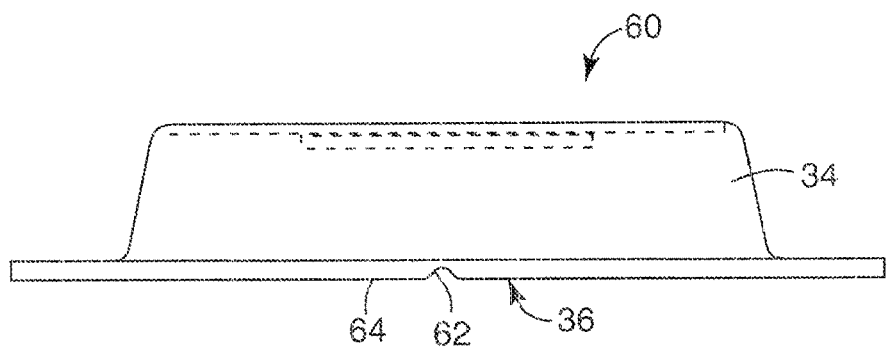
FIG. 6 is a side view of another embodiment of a microneedle patch having a channel defined therethrough.

The embodiment of openings or passageways shown in FIGS. 4 and 5 are merely exemplary, and other means of providing openings are possible. For instance, FIG. 6 is a side view of a portion of another embodiment of a microneedle patch 60 having a channel 62 defined therethrough. The channel 62 is substantially an inverted U-shape and disposed in a perimeter lip 36, along a bottom, skin contacting face 64 of the perimeter lip 36. The channel 62 creates a generally radially extending opening or passageway that permits air to escape from the interior volume of the patch 60 as it collapses. The size of the channel can be selected according to the amount of airflow desired during collapse of the patch 60. One or more channels can be included, as desired.

Figure 7:
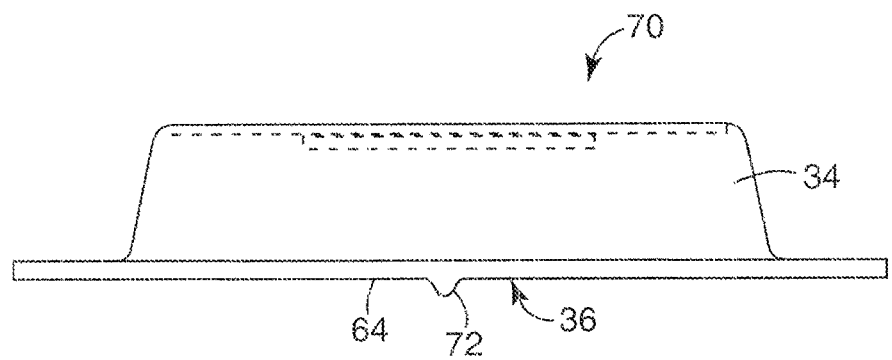
FIG. 7 is a side view of another embodiment of a microneedle patch having a rib disposed thereon.

FIG. 7 is a side view of a portion of another embodiment of a microneedle patch 70 having a rib 72 disposed thereon. The rib 72 can be a protrusion extending from a bottom, skin-contacting face 64 of a perimeter lip 36 of the patch 70. The rib 72 is elongate, and extends generally radially along the perimeter lip 36. In further embodiments, the rib 72 can have nearly any shape, and nearly any number of ribs can be included. When the skin-contacting face 64 of the perimeter lip 36 is positioned against a surface (e.g., against the skin of a patient or test subject), the rib 72 spaces at least a portion of the surface from the skin-contacting face 64 of the perimeter lip 36. This creates a passageway adjacent the rib 72 that permits air to escape from the interior volume of the patch 70 as it collapses. The height of the rib 72 can be selected according to the amount of airflow desired during collapse of the patch 70.

Figure 8:
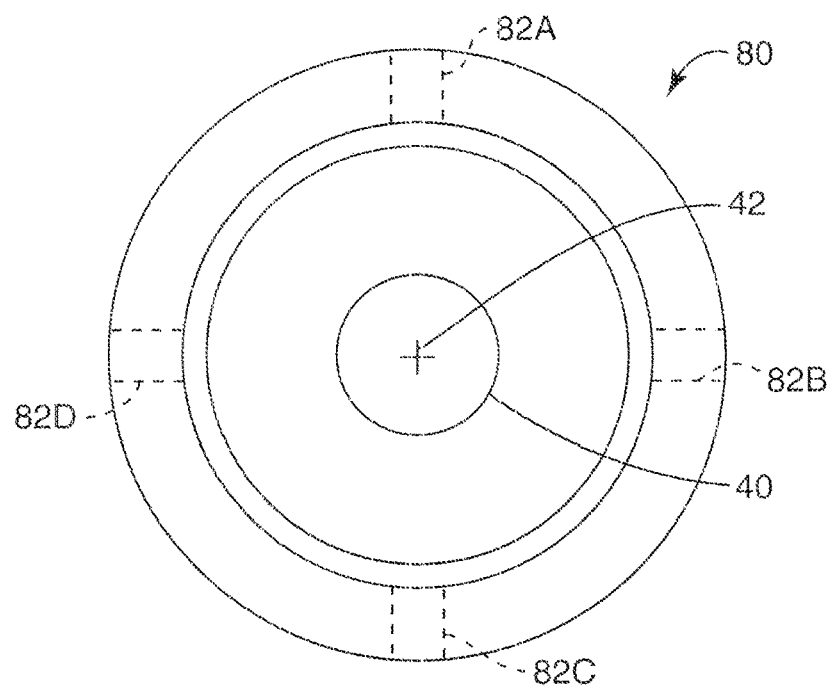
FIG. 8 is a bottom view of a microneedle patch showing possible venting feature locations.

FIG. 8 is a bottom view of a microneedle patch 80 showing possible feature locations 82A-82D. Airflow features such as those shown and described with respect to FIGS. 6 and 7 can be disposed at any or all of the locations 82A-82D. As shown in FIG. 8, the airflow features (at locations 82A-82D) can extend generally radially along the perimeter lip 36, relative to axis 42. Other feature locations are possible, as those shown in FIG. 8 are merely exemplary.

Figure 19:
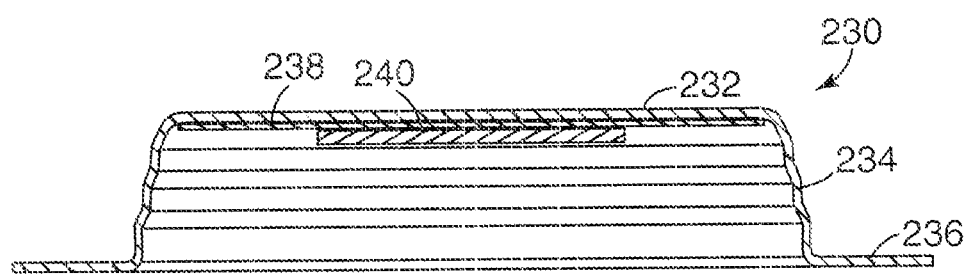
FIG. 19 is a cross-sectional view of another embodiment of a microneedle patch in an expanded state.
Figure 20:
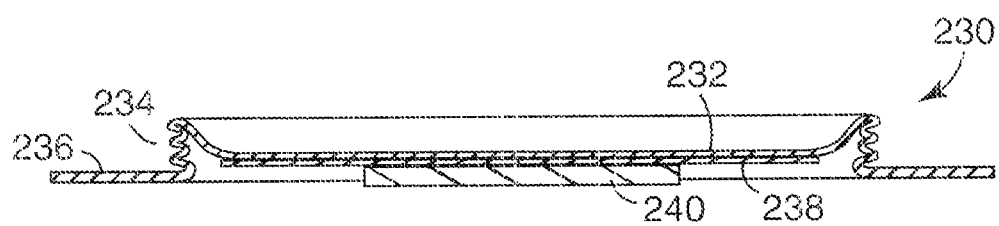
FIG. 20 is a cross-sectional view of another embodiment of a microneedle patch in a collapsed state.

FIG. 19 is a cross-sectional view of another embodiment of a microneedle patch in an expanded state. The microneedle patch 230 has a collapsible patch element comprising a generally circular base portion 232, at least one side wall 234 extending from the base portion 232, and a perimeter lip 236 extending from the side wall 234 opposite the base portion 232. The base portion 232, the side wall 234 and the perimeter lip 236 can be formed integrally. An adhesive 238 is disposed on the base portion 232, and a microneedle array 240 is supported by the base portion 232 (individual microneedles of the array 240 are not visible in the figures). The side wall 234 is generally perpendicular to the base 232 and the lip 236, such that the inner diameter of the perimeter lip 236 is about the same size as the perimeter of the base portion 232. As seen in FIG. 19, the side wall 234 is pleated, such that it can fold in a manner similar to an accordion. FIG. 20 is a cross-sectional view of the microneedle patch 230 in the collapsed state where the pleats have been pressed against one another.

In order to store and transport microneedle arrays and microneedle patches, packages according to the present invention can be provided. These packages offer protection to microneedle arrays that are often fragile and contamination-sensitive. In addition, these packages permit storage of the collapsible microneedle patches while reducing the risk of undesired patch collapse, due to inadvertent contact or other factors.

Figure 9:
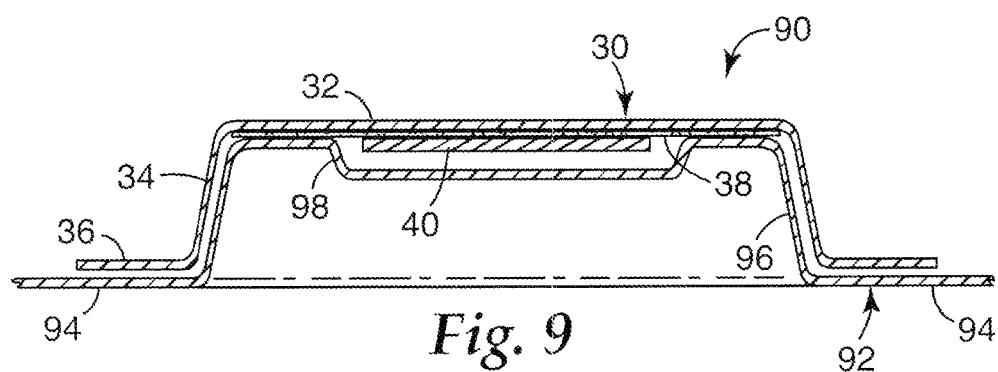
FIG. 9 is a cross-sectional view of a microneedle patch assembly.

FIG. 9 is a cross-sectional view of a microneedle patch assembly 90 that includes a microneedle patch 30 and a carrier 92 that together form a closed package. The carrier 92 includes a base portion 94, a raised portion 96, and a recess 98 disposed in the raised portion 96. The patch 30 is positioned on the carrier 92, such that the raised portion 96 of the carrier 92 extends at least partially into the volume defined between the base 32 and the side wall 34 of the patch 30. Thus the raised portion 96 of the carrier 92 may be considered to mate with the patch 30. The recess 98 extends toward the base portion 94 of the carrier 92, creating a volume into which the microneedle array 40 can extend. This permits the base portion 94 of the carrier 92 to contact the perimeter lip 36 of the patch 30 and the raised portion 96 to contact the side wall 34 and the base 32 (or adhesive 38 disposed on the base 32) of the patch 30 without the carrier 92 contacting the microneedle array 40. However, the carrier can be shaped in other ways. For instance, the raised portion 96 need not come into contact with the base 32 (or adhesive 38 disposed on the base 32) of the patch 30.

A number of discrete raised portions 96 can extend from a single base portion 94 of the carrier 92. This permits a plurality of individual patches 30 to be carried on a single carrier 92. In addition, the carrier 92 can be optionally adhered to the patch 30, for example, by the adhesive 38. In further embodiments, the carrier 92 can be adhered to the patch 30 with adhesive disposed on the perimeter lip 36. The portion 94 of the carrier 92 that contacts the perimeter lip 36 of the patch 30 may be a release or non-stick surface, such that the adhesive of the patch may be easily removed from it. This may be achieved by suitable selection of adhesive and carrier material or it may be desirable to provide a release coating, such as a low surface energy silicone, fluoropolymer, or fluoro-silicone release coating on the carrier 92.

The carrier 92 is separable from the patch 30. The patch 30 can be positioned on the carrier 92 for storage and transportation. The carrier 92 is then removed from the patch 30 prior to application of the patch 30 to a patient. Because the carrier 92 is only disposed relative to one side of the patch 30, an operator can pick up the patch 30 and separate it from the carrier 92 either manually or with a tool such as a patch applicator device. The carrier 92 is typically formed so as to be relatively rigid. Suitable materials include polymers, such as polypropylene, polybutylene terephthalate, polystyrene, polyethylene, polythermide, polyethylene terephthalate, polystyrene, polyvinyl chloride, polymethylmethacrylate, acrylonitrile-butadiene styrene, polycarbonate, and blends thereof. The carrier may be formed from the same material as the collapsible patch element, but the carrier thickness will typically be greater than the thickness of part or all of the patch element. Rigidity of the carrier 92 offers protection to the patch 30 from undesired collapse, and from damage and contamination.

Figure 10:
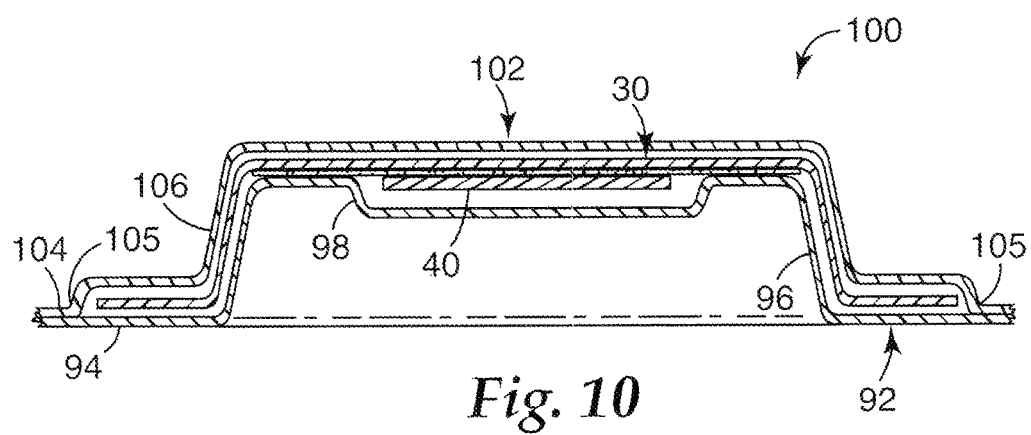
FIG. 10 is a cross-sectional view of another embodiment of a microneedle patch assembly.

FIG. 10 is a cross-sectional view of another embodiment of a microneedle patch assembly 100. The assembly 100 includes a patch 30, a (first) carrier 92, and a second carrier 102 that together form a package. The patch 30 and the carrier 92 are similar to those shown and described with respect to FIG. 9. The second carrier 102 includes a base portion 104 and a raised portion 106 extending from the base portion 104. The patch 30 is disposed on the (first) carrier 92, and the second carrier 102 is disposed on or over the patch 30, opposite the (first) carrier 92. The raised portion 106 of the second carrier 102 defines a volume into which the patch 30 can extend. The raised portion 96 of the (first) carrier 92 can also extend into the volume defined by the raised portion 106 of the second carrier 102. The (first) carrier 92 and the second carrier 102 can be sealed or adhered together about their respective peripheries (such as at location 105 in FIG. 10) in order to better protect the patch 30 for contamination and other damage, as well as to better preserve any substances (e.g., pharmaceuticals) carried by the microneedle array 40. Sealing may be by any suitable means, such as by use of an adhesive or a heat seal. In one embodiment a hermetic seal is provided to protect the patch from environmental influences so that the patch may be stored, for example, while maintaining sterility. Both carriers may be separable from the patch and one or both may be removed by hand or with the aid of an applicator device. They may be removed in any order or they may be removed simultaneously. The second carrier is generally formed so as to be relatively rigid and in one embodiment may be formed from the same material as the first carrier.

Figure 11:
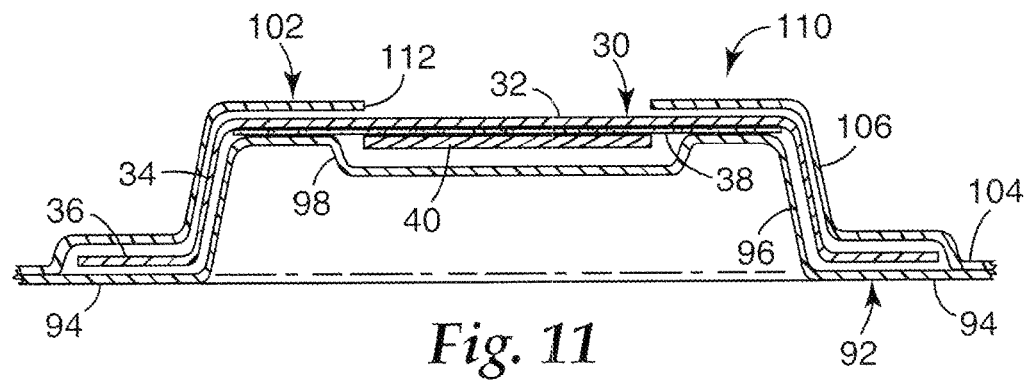
FIG. 11 is a cross-sectional view of another embodiment of a microneedle patch assembly.

FIG. 11 is a cross-sectional view of another embodiment of a microneedle patch assembly 110. The assembly 110 is similar to that shown and described with respect to FIG. 10. However, in this embodiment, an opening 112 is defined through a center region of the raised portion 106 of the second carrier 102. The opening 112 permits access to the patch 30 near the microneedle array 40. The opening 112 can allow a portion of a patch applicator device to contact the base 32 of the patch 30 above the microneedle array 40 to apply a force, which can collapse the patch 30 and move the microneedle array 40 toward a target site (after the (first) carrier 92 is removed). Prior to deployment of the microneedle array 40, for storage and transportation, the opening 112 can be covered and sealed, for instance, with foil or other type of removable cover. In the embodiment shown in FIG. 11 the second carrier may be removed after collapse of the patch while allowing the patch to remain in contact with the target surface. Alternatively, the second carrier may stay in place on the target surface until removal of the patch.

Figure 12:
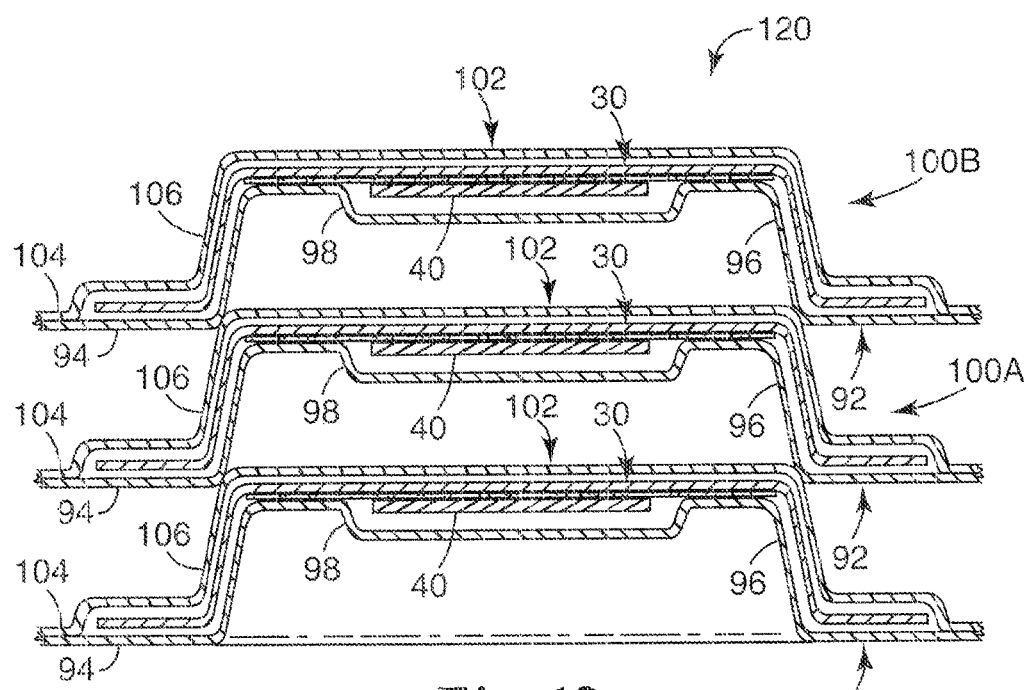
FIG. 12 is a cross-sectional view of a stack of nested microneedle patch assemblies.

A number of patch assemblies can be arranged together as a package. FIG. 12 is a cross-sectional view of a stack 120 of a plurality of nested microneedle patch assemblies 100 that forms a package. The raised portion 106 of the second carrier 102 of one patch assembly 100A extends into the volume defined by the raised portion 96 of the (first) carrier 92 of an adjacent patch assembly 100B. Almost any number of patch assemblies 100 can be nested together. Moreover, different types of patch assemblies can be stacked together. The stack 120 facilitates storage and transportation of patch assemblies.

In operation, a patch 30 according to the present invention can be applied to a target location using an applicator device. Examples of suitable microneedle application devices are disclosed in International Patent Publication WO 05/123173 and U.S. Patent Application Publication No. 2002-0087182, which are hereby incorporated by reference in their entirety. However, a variety of patch applicators can be used to apply the patch 30.

Figure 13:
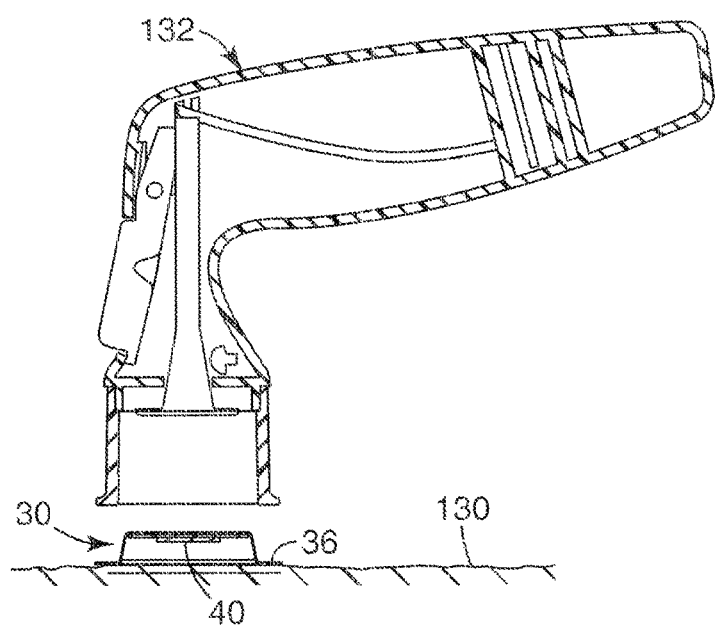
FIG. 13 is a cross-sectional view of a microneedle patch according to the present invention adhered to an application surface, and a microneedle patch applicator.

A first method of applying a patch includes adhering the patch to a surface and then bringing an applicator device to the patch for activation. FIG. 13 is a cross-sectional view of a microneedle patch 30 in an expanded state adhered to an application surface 130, and a microneedle patch applicator 132 spaced from the patch 30. The patch 30 can be adhered to the application surface 130, for example, by adhesive disposed on the perimeter lip 36 of the patch 30. Once the microneedle patch 30 is in place on the application surface 130, the microneedle patch applicator 132 can be placed over the patch 30. A collar portion 134 can then engage the patch 30, and, in one embodiment, may include one or more vent cutters thereon for cutting through a portion or portions of the patch 30 to form vent openings therethrough. The patch applicator 132 is activated, as explained below, to engage the microneedle array 40 with the application surface 130. It should be understood that after the patch is adhered to the target surface it may simply be pressed manually to engage the microneedle array with the application surface. Manual application, however, may not be as reproducible as that obtained with an appropriately configured applicator device.

Figure 14:
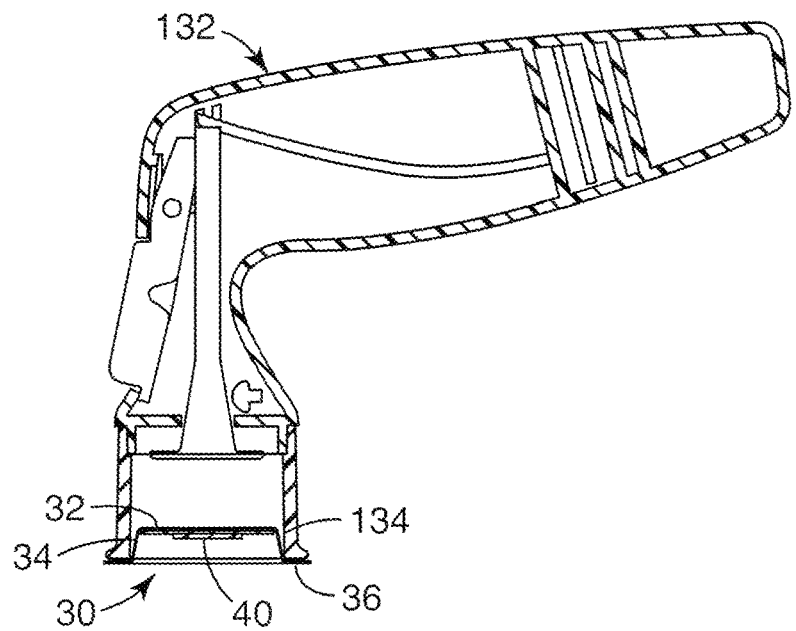
FIG. 14 is a cross-sectional view of a microneedle patch according to the present invention held in a microneedle patch applicator.

Another method of applying a patch includes placing the patch on or in an applicator device before either is positioned near an application surface. FIG. 14 is a cross-sectional view of a microneedle patch 30 in an expanded state held on a microneedle patch applicator 132. The patch applicator 132 has an outer collar portion 134, which can be cylindrical in shape or have another shape that corresponds to a shape of the patch 30. The perimeter lip 36 of the patch 30 can rest against a bottom portion of the collar 134 of the applicator device 132, and the side wall 34 and base 32 of the patch 30 can extend into an interior portion of the collar 134. In this position, the microneedle array 40 of the patch 30 is generally disposed in the interior portion of the collar 134 of the applicator device 132.

Figure 15:
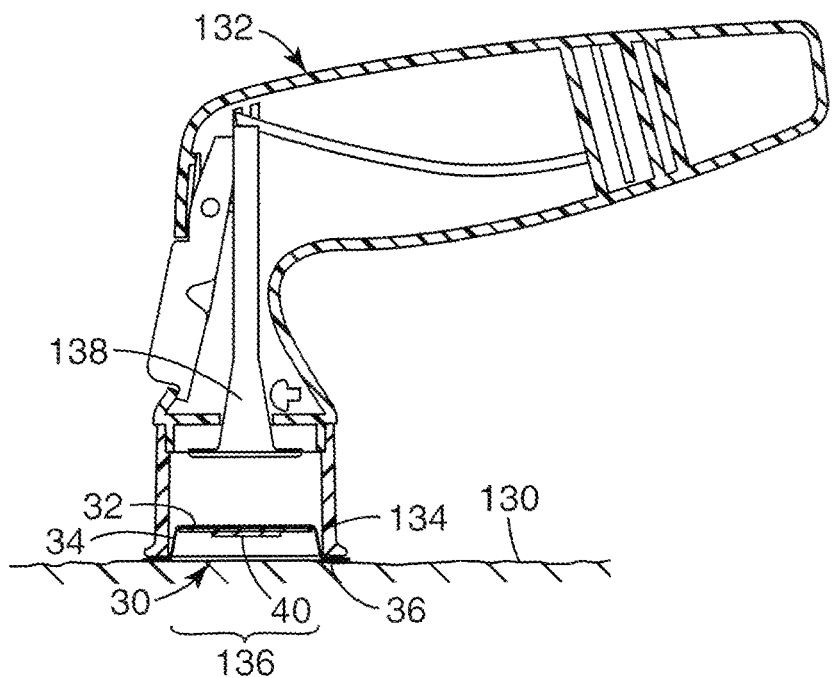
FIG. 15 is a cross-sectional view of a microneedle patch according to the present invention positioned relative to an application surface prior to microneedle deployment, and a microneedle patch applicator.

Once the patch 30 is placed in or on the applicator device 132, according to the methods described with respect to FIGS. 13 and 14 or by other methods, the patch 30 and applicator device 132 are both positioned to deploy the microneedle array 40 of the patch 30. FIG. 15 is a cross-sectional view of a microneedle patch 30 in an expanded state held on a microneedle patch applicator 132, with both the patch 30 and the applicator 132 positioned relative to an application surface 130 prior to microneedle array 40 deployment to a target site 136. As shown in FIG. 15, a patch accelerator 138 of the applicator device 132 is spaced from the patch 30 and has not yet contacted or moved the patch 30.

Figure 16:
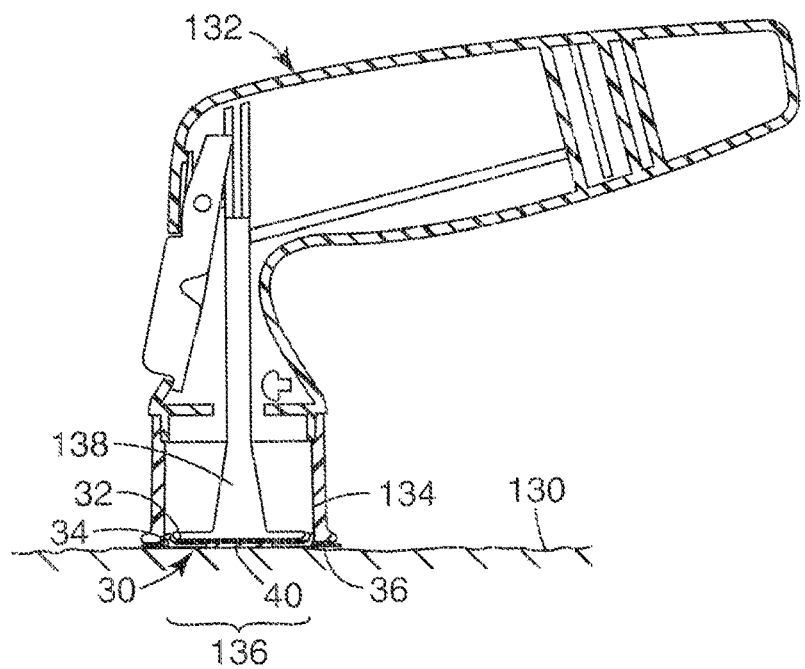
FIG. 16 is a cross-sectional view of a microneedle patch according to the present invention positioned relative to an application surface after microneedle deployment, and a microneedle patch applicator.

After the patch 30 and the applicator 132 are positioned relative to the target site 136, the microneedle array 40 can be deployed. FIG. 16 is a cross-sectional view of the microneedle patch 30 in a collapsed state after deployment of the microneedle array 40 to the target site 136 on the application surface 130 by the microneedle patch applicator 132. The microneedle array 40 has been moved into contact with the application surface 130 by the patch accelerator 138. The patch 30 can be adhered to the application surface 130 with an adhesive 38 disposed on the base 32 of the patch 30, as desired.

Figure 17:
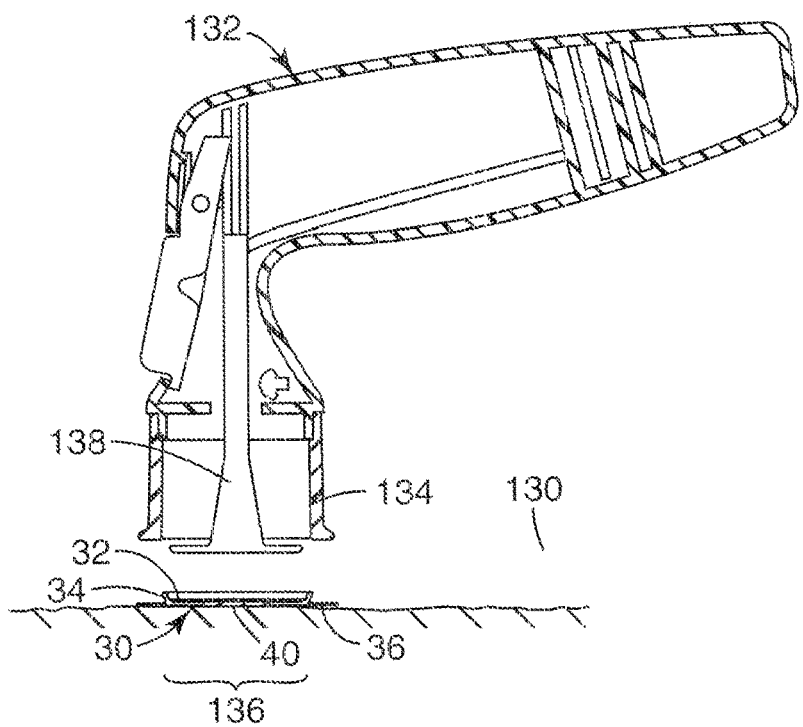
FIG. 17 is another cross-sectional view of a microneedle patch according to the present invention adhered to an application surface after microneedle deployment, and a microneedle patch applicator.

After the microneedle array 40 of the patch 30 is deployed, the patch 30 can remain in contact with the application surface 130 while the applicator device 132 is moved away. FIG. 17 is a cross-sectional view of the microneedle patch 30 adhered to the application surface 130 after microneedle array 40 deployment, with the microneedle patch applicator 132 spaced from the patch 30 (i.e., the collar 134 of the applicator device 132 does not contact the patch 30).

In one embodiment, an applicator will accelerate the microneedle array 40 to a desired velocity that is effective to pierce the microneedles into the skin. The desired velocity is preferably controlled to limit or prevent stimulation of the underlying nerve tissue. The maximum velocity achieved by the microneedle array upon impact with the skin is often 20 meters per second (m/s) or less, potentially 15 m/s or less, and possibly 10 m/s or less. In some instances, the maximum velocity may be 8 m/s or less. In other instances, the minimum velocity achieved by the microneedle array upon impact with the skin is often 2 m/s or more, potentially 4 m/s or more, and possibly 6 m/s or more.

Figure 18:
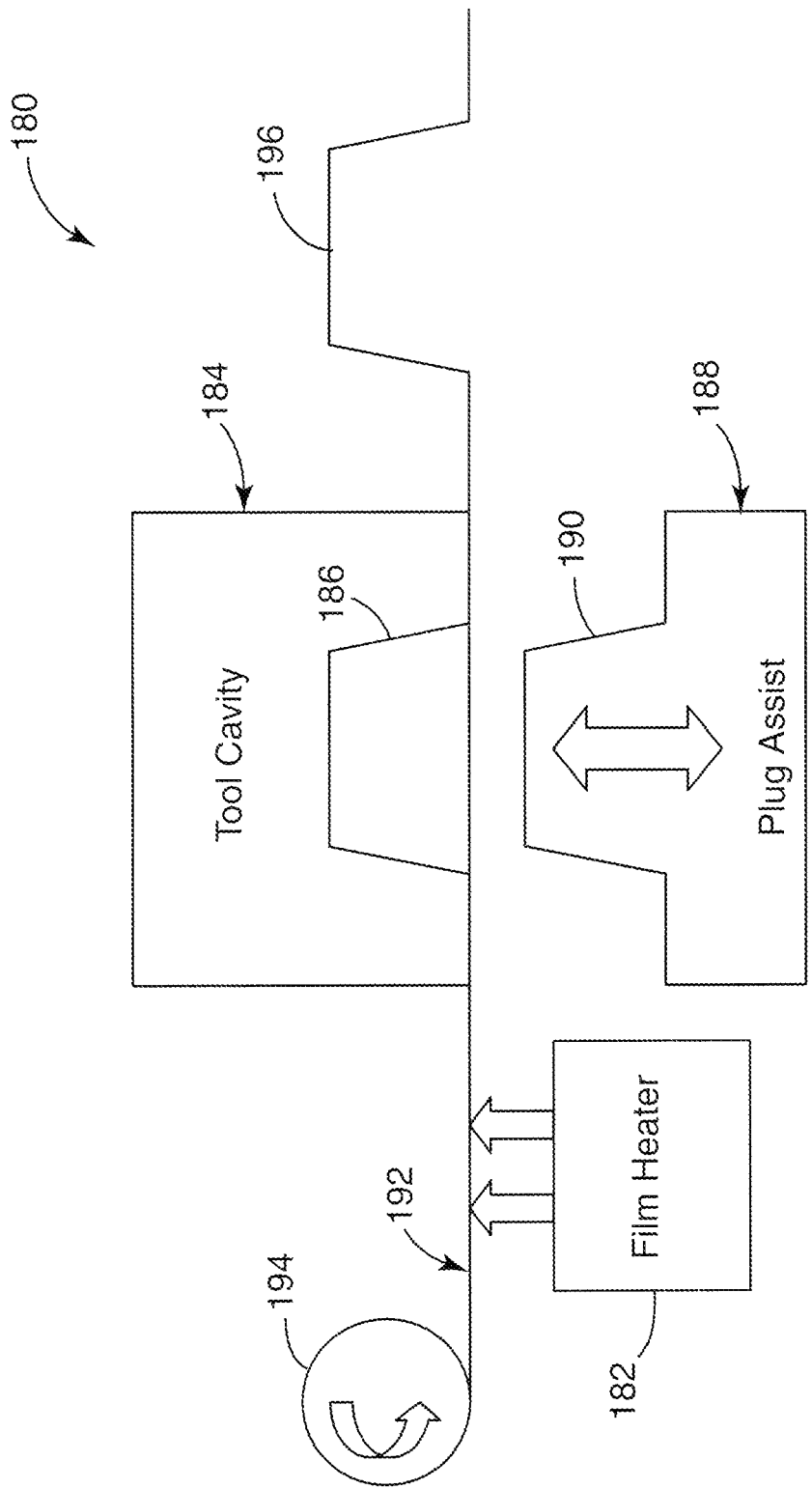
FIG. 18 is a schematic representation of a manufacturing system for producing microneedle patches according to the present invention.

FIG. 18 is a schematic representation of a manufacturing system 180 for producing microneedle patches according to the present invention. The system 180 includes a film heater 182 and a die tool 184 having at least one cavity 186. Additional cavities can be provided in the die tool 184. In the embodiment shown in FIG. 18, the system 180 further includes a movable plug 188 having an engagement portion 190 for cooperatively engaging the cavity 186 of the die tool 184. In further embodiments, the die tool 184 can utilize a vacuum forming assembly either in addition to or in place of plug assist from the plug 188.

In operation, a web of material 192 is provided. The web of material 192 can be in the form of a film from a roll 194 of film stock. First, the web of material 192 is unrolled, and is heated by the film heater 182. This heating helps prepare the web of material 192 for being formed into a three-dimensional shape by making it more readily deformable. Next, a portion of the heated web of material 192 is positioned at the cavity 186 of the die tool 184, between the die tool 184 and the plug 188. The plug 188 moves toward the die tool 184 such that the engagement portion 190 of the plug and the cavity 186 of the die tool 184 cooperatively deform the web of material 192 to form at least one collapsible patch (e.g., collapsible patch 30 shown and described with respect to FIGS. 1-2B and 3A-3B). Then the plug 188 is moved away from the die tool 184. A formed patch element 196 of the web of material 192, formed with the die tool 184 and plug 188, is then moved away from the die tool 184.

Additional patch elements can be formed on the web of material 192 in a similar fashion as that described above. The individual patch elements can be separated from each other after they have been formed, or the patch elements can remain connected for transportation and further processing (e.g., for connecting microneedle arrays and or for affixing adhesive to a portion of the lower face of the web material).

In one embodiment, a microneedle array may be formed directly on the web of material 192 during a forming step that can take place before, after, or concurrent with the plug forming step. Additional details regarding molding processes suitable for forming a microneedle array as part of a web may be found in U.S. patent application Ser. No. 60/753,808, filed Dec. 23, 2005, the disclosure of which is herein incorporated by reference.

The microneedle arrays useful in the various embodiments of the invention may comprise any of a variety of configurations, such as those described in the following patents and patent applications, the disclosures of which are herein incorporated by reference. One embodiment for the microneedle arrays comprises the structures disclosed in United States Patent Application Publication No. 2003/0045837. The disclosed microstructures in the aforementioned patent application are in the form of microneedles having tapered structures that include at least one channel formed in the outside surface of each microneedle. The microneedles may have bases that are elongated in one direction. The channels in microneedles with elongated bases may extend from one of the ends of the elongated bases towards the tips of the microneedles. The channels formed along the sides of the microneedles may optionally be terminated short of the tips of the microneedles. The microneedle arrays may also include conduit structures formed on the surface of the substrate on which the microneedle array is located. The channels in the microneedles may be in fluid communication with the conduit structures. Another embodiment for the microneedle arrays comprises the structures disclosed in U. S. Patent Application Publication No. 2005/0261631, which describes microneedles having a truncated tapered shape and a controlled aspect ratio. Still another embodiment for the microneedle arrays comprises the structures disclosed in U.S. Pat. No. 6,091,975 (Daddona, et al.) which describes blade-like microprotrusions for piercing the skin. Still another embodiment for the microneedle devices comprises the structures disclosed in U.S. Pat. No. 6,312,612 (Sherman, et al.) which describes tapered structures having a hollow central channel. Still another embodiment for the micro arrays comprises the structures disclosed in U.S. Pat. No. 6,379,324 (Gartstein, et al.) which describes hollow microneedles having at least one longitudinal blade at the top surface of tip of the microneedle.

Microneedle patches of the present invention may be used to deliver drugs (including any pharmacological agent or agents) through the skin in a variation on transdermal delivery, or to the skin for intradermal or topical treatment, such as vaccination.

In one aspect, drugs that are of a large molecular weight may be delivered transdermally. Increasing molecular weight of a drug typically causes a decrease in unassisted transdermal delivery. Microneedle patches of the present invention have utility for the delivery of large molecules that are ordinarily difficult to deliver by passive transdermal delivery. Examples of such large molecules include proteins, peptides, nucleotide sequences, monoclonal antibodies, DNA vaccines, polysaccharides, such as heparin, and antibiotics, such as ceftriaxone.

In another aspect, microneedle patches of the present invention may have utility for enhancing or allowing transdermal delivery of small molecules that are otherwise difficult or impossible to deliver by passive transdermal delivery. Examples of such molecules include salt forms; ionic molecules, such as bisphosphonates, preferably sodium alendronate or pamedronate; and molecules with physicochemical properties that are not conducive to passive transdermal delivery.

In another aspect, microneedle patches of the present invention may have utility for enhancing delivery of molecules to the skin, such as in dermatological treatments, vaccine delivery, or in enhancing immune response of vaccine adjuvants.

Microneedle patches may be used for immediate delivery, that is where they are applied and immediately removed from the application site, or they may be left in place for an extended time, which may range from a few minutes to as long as 1 week. In one aspect, an extended time of delivery may be from 1 to 30 minutes to allow for more complete delivery of a drug than can be obtained upon application and immediate removal. In another aspect, an extended time of delivery may be from 4 hours to 1 week to provide for a sustained release of drug.

Although the present invention has been described with reference to several alternative embodiments, workers skilled in the art will recognize that changes may be made in form and detail without departing from the spirit and scope of the invention. For instance, various types of microneedle arrays can be utilized according to the present invention.

The invention claimed is:

1. A method of microneedle array deployment, the method comprising:
positioning a patch that comprises a base, at least one collapsible side wall extending from the base, and a perimeter lip extending radially outward from the collapsible side wall opposite the base and that carries a microneedle array relative to an application surface such that at least a portion of the perimeter lip contacts the application surface; and
collapsing at least a portion of the patch while moving the microneedle array toward a target site, wherein collapsing at least a portion of the patch comprises causing the at least one collapsible side wall to fold upon itself.

2. The method of claim 1, and further comprising:
adhering the patch to the application surface with an adhesive prior to collapsing the patch.

3. The method of claim 2, wherein the adhesive is disposed on at least a portion of the perimeter lip.

4. The method of claim 1, wherein the collapsible side wall has a thickness, the perimeter lip has a thickness, and the base has a thickness, and further wherein the thickness of the collapsible side wall is smaller than the thickness of the base portion, and further wherein the thickness of the collapsible side wall is smaller than the thickness of the perimeter lip.

5. The method of claim 1, wherein the collapsible side wall has a thickness of about 0.00254 mm to about 0.254 mm.

6. The method of claim 1, wherein the base has a thickness of about 0.127 mm to about 1.27 mm.

7. The method of claim 1, wherein the perimeter lip has a thickness of about 0.127 mm to about 1.27 mm.

8. A method of microneedle array deployment, the method comprising:
positioning a patch carrying a microneedle array on an application surface near a target site, wherein the patch is initially in an expanded state and the microneedle array is spaced from the target site, and wherein the patch comprises a base carrying the microneedle array, at least one collapsible side wall extending from the base, and a perimeter lip extending radially outward from the collapsible side wall opposite the base, wherein positioning the patch comprises contacting at least a portion of the perimeter lip with the application surface;

moving the microneedle array toward the target site by placing the patch in a collapsed state where at least a portion of the patch is collapsed such that the at least one collapsible side wall folds upon itself and the microneedle array contacts the target site; and adhering the patch to the target site with an adhesive disposed on the patch.

9. The method of claim 8, wherein the adhesive is disposed on at least a portion of the perimeter lip.

\* \* \* \* \*